(12) United States Patent
Prout

(10) Patent No.: US 11,178,956 B1
(45) Date of Patent: Nov. 23, 2021

(54) SYSTEM, METHOD AND MOBILE APPLICATION FOR COSMETIC AND SKIN ANALYSIS

(71) Applicant: Andrew Lawrence Prout, Edmonds, WA (US)

(72) Inventor: Andrew Lawrence Prout, Edmonds, WA (US)

( * ) Notice: Subject to any disclaimer, the term of this patent is extended or adjusted under 35 U.S.C. 154(b) by 323 days.

(21) Appl. No.: 16/172,943

(22) Filed: Oct. 29, 2018

(51) Int. Cl.
   *A45D 44/00*   (2006.01)
   *A61B 5/00*    (2006.01)

(52) U.S. Cl.
   CPC ...... *A45D 44/005* (2013.01); *A45D 2044/007* (2013.01); *A61B 5/441* (2013.01); *G06T 2207/10004* (2013.01)

(58) Field of Classification Search
   None
   See application file for complete search history.

(56) References Cited

U.S. PATENT DOCUMENTS

| | | | |
|---|---|---|---|
| 2008/0194928 A1* | 8/2008 | Bandic | A61B 5/442 600/306 |
| 2009/0245603 A1* | 10/2009 | Koruga | A61B 5/445 382/128 |
| 2014/0146190 A1* | 5/2014 | Mohammadi | A61B 5/0077 348/207.2 |
| 2015/0356661 A1* | 12/2015 | Rousay | G06Q 30/0631 705/26.7 |
| 2017/0178220 A1* | 6/2017 | Chong | G06K 9/00268 |
| 2018/0060919 A1* | 3/2018 | Gu | H04L 67/02 |

* cited by examiner

*Primary Examiner* — Jason T Yen
(74) *Attorney, Agent, or Firm* — Hanrahan Law Firm, P.A.; Benjamin M. Hanrahan

(57) ABSTRACT

A system, method and application for analyzing one or more facial images of a user's face, and providing cosmetic and skin care recommendations is presented herein. Specifically, the system and method is structured to generate a baseline facial model that represents the user's ideal look and cosmetic application. When the user uploads a new facial photograph, the system and method processes that facial photograph against the baseline facial model to provide cosmetic recommendations, allowing for a consistent and desired cosmetic application. A skin analysis engine is also included to receive and process a plurality of historical images or photographs of the user's face and to identify one or more skin properties, such as wrinkles, lines and pores thereon. The skin analysis engine compares historical facial images to provide progress reports and analyses.

17 Claims, 24 Drawing Sheets

200
Baseline Facial Model Creation Engine

Scan face with "ideal" cosmetic application
user takes a photograph of his or her face
with the camera or image capturing device, or
user uploads a previously captured photograph
of his or her face,
the photograph representing a desirable
or ideal application of cosmetics or skin care products.. — 202

Select Celebrity, Model or Other Provided Sample(s)
User selects one or more images
of other individuals with different make-up,
cosmetic or skin care product
applications, styles or techniques — 204

Create Baseline Facial Model
and save to user's profile or account — 206

FIG. 3

SYSTEM, METHOD AND MOBILE APPLICATION FOR COSMETIC AND SKIN ANALYSIS

FIELD OF THE INVENTION

The present invention is generally directed to a system, method and mobile-based application for providing skin and cosmetic analysis, instructions and recommendations. In some embodiments, the analysis, instructions or recommendations may be based upon an "ideal" baseline or a plurality of historical images.

BACKGROUND OF THE INVENTION

The variety and number of available cosmetics, skin care products and the like are vast, and to some people, daunting or intimidating. As just an example, when choosing an eye liner, there are different categories or types of eye liners, such as gel eye liners, pencil eye liners and liquid eye liners. Within each of these categories there are an extraordinary amount of colors, shades, brands, consistencies, etc., some of which may look better or work better on some people, while others will work better or look better on other people.

Similarly, when choosing skin care products, such as anti-wrinkling cream or anti-aging products, there are a vast amount of varieties, consistencies, brands, etc., each of which may have different benefits for different people.

Many people find it extremely difficult to not only find the right products for their desired cosmetic or skin care goals, but also to consistently apply those cosmetics to their face or skin in order to achieve the ideal results on a consistent basis.

There is thus a need in the art for a novel cosmetic and skin care analysis system, method and application that would be able to analyze or process cosmetic application to a user's face, and consistently and reliably provide recommendations as to what product(s) to use and how to use them. It would also be beneficial if the proposed system, method and application is able to track and compare historical images of the user, for example, of the user's face, and generate skin care reports based on those historical images. Such a report would help the user determine whether a particular skin care product or skin care routine was working as anticipated or desired.

SUMMARY OF THE INVENTION

Accordingly, the present invention is generally directed to a system, method and application for analyzing or processing one or more facial images, for example, images of the user's face, and providing cosmetic and skin care recommendations. The present invention may be embodied in a mobile application that can be downloaded and installed on a user's mobile device, such as a smartphone or tablet. However, other embodiments may be in the form of a website, desktop application, or the like.

In any event, at least one embodiment of the present invention may generate or create a baseline facial model that represents the user's ideal or desired look. The baseline facial model may be based upon one or more of the following: (a) an image of the user's face that includes make-up or other cosmetic application of which the user believes is desirable (e.g., an image or photograph of the user representing an ideal or near perfect application of cosmetics or skin care products to the user's face), (b) preferences selected or identified by the user, such as preferences in a type or brand of cosmetics, style, color, technique, etc. and/or (c) one or more selected images of celebrities, models, or other people who have different cosmetics or cosmetic techniques applied to their face.

Using these various criteria, and using an artificial intelligence engine, at least one embodiment of the present invention is structured and configured to generate a baseline facial model of the user's face and cosmetic application. This may be conducted or generated by virtue of an artificial intelligence (AI) engine, including but in no way limited to IBM's WATSON, another similar AI engine or a newly created AI engine. In any event, the baseline facial model created will be used as a bar or baseline whenever the user scans his or her face and seeks recommendations or instructions on how to achieve the ideal look or cosmetic application.

In addition, at least one embodiment of the present invention will also implement a skin analysis engine, which may be implemented by IBM WATSON, another similar AI engine or a newly created engine within the scope of the present invention. The skin analysis engine will operate to receive and process a plurality of historical images or photographs of the user's face in order to identify one or more skin properties thereon. The skin properties can include, but are in no way limited to wrinkles, fine lines, clarity, dark circles, dark spots, red spots, pores, etc.

More in particular, the skin analysis engine can be used to track progress of the user's skin over time, for example, to determine whether a skin care product or skin care regime is effective.

These and other objects, features and advantages of the present invention will become more apparent when the drawings as well as the detailed description are taken into consideration.

BRIEF DESCRIPTION OF THE DRAWINGS

FIG. 3 is a high-level flow chart illustrating the baseline facial model creation engine in accordance with at least one embodiment of the system and method disclosed herein.

Like reference numerals refer to like parts throughout the several views of the drawings provided herein.

DETAILED DESCRIPTION OF THE INVENTION

As shown in the accompanying drawings, the present invention is generally directed to a system, method and mobile application for providing skin and cosmetic analysis, instructions and recommendations. In particular, as will be described herein, a user of at least one embodiment of the present invention will be provided with instructions to apply cosmetics, for example, based on a "ideal" or baseline model. In other embodiments, the system, method and application of the present invention is configured to receive, process and analyze a plurality of images of the user's face and provide an identification and historical analysis of one or more properties, such as wrinkles, lines, spots, circles, pores, etc.

In particular, FIGS. 1 through 6 illustrate various methods and flow charts of various features and methods of the present invention, whereas FIGS. 7 through 24 illustrate various exemplary screenshots of the mobile application that can be used to implement certain features described herein. For illustrative purposes, the flowcharts and methods of FIGS. 1 through 6 can be viewed in conjunction with the exemplary screenshots of FIGS. 7 through 24, as explained herein.

Figure 1:
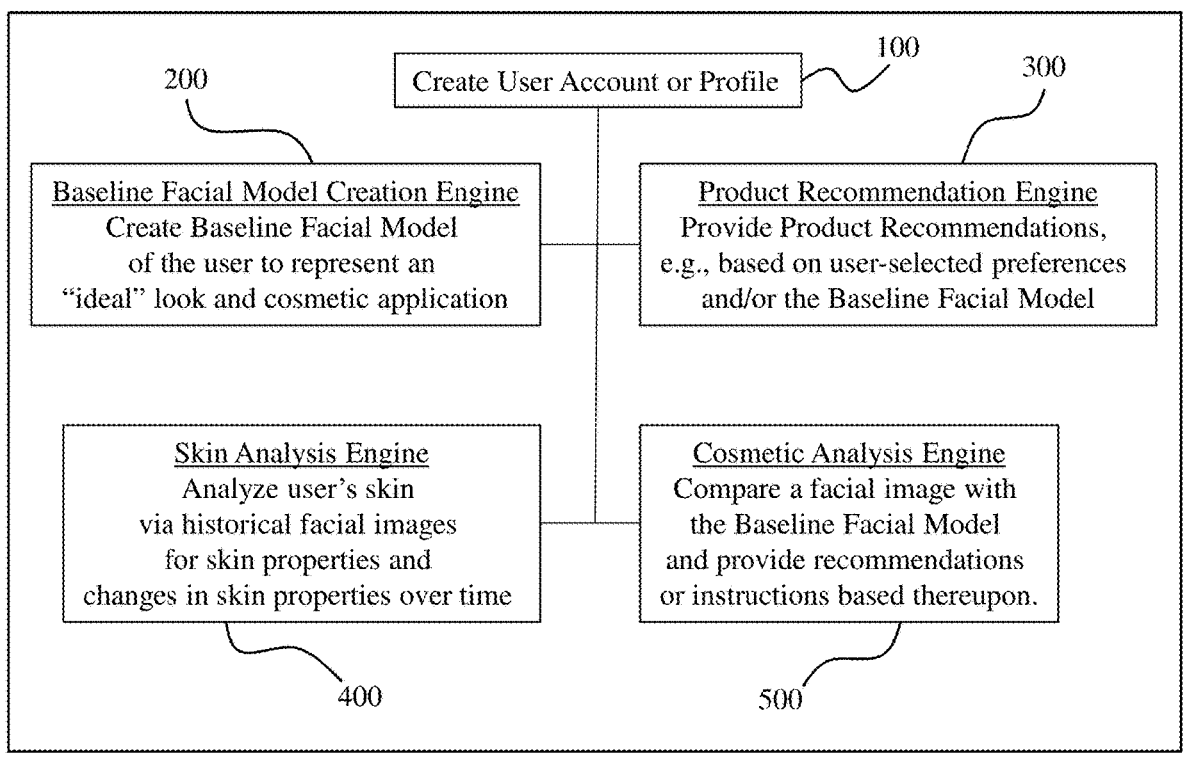
FIG. 1 is a block diagram illustrating various features and engines of at least one embodiment of the system and method disclosed herein.
Figure 7:
FIG. 7 is an exemplary screenshot of the application of at least one embodiment of the present invention illustrating the account and profile creation as disclosed herein.
Figure 8:
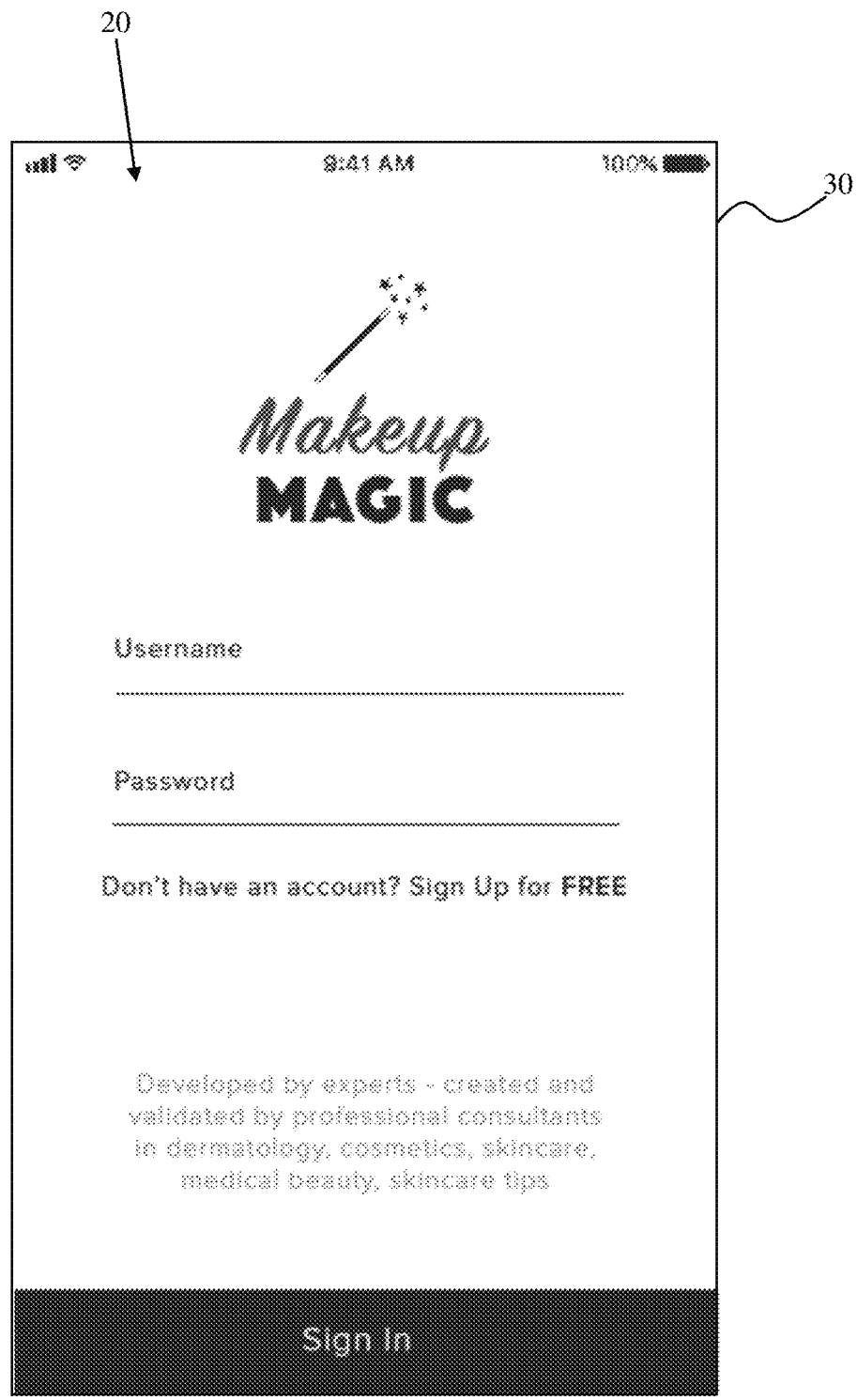
FIG. 8 is an exemplary screenshot of the application of at least one embodiment of the present invention illustrating the account and profile creation as disclosed herein.

Specifically, with reference to the high-level flowchart of FIG. 1, a plurality of features and/or capabilities of the method 50 and application 20 of the present invention are illustrated. For example, in at least one embodiment a user or participant of the system, method or application may first create an account, as generally represented at 100. For instance, the system and method of at least one embodiment may be implemented within or via a mobile application 20, which can be accessed by a mobile user device 30. With reference to FIGS. 7 and 8, reference character 30 generally represents at least a portion of the mobile user device 30, such as the display screen or display area thereof. Accordingly, the mobile user device 30, as used herein, may include a smartphone (e.g., APPLE® iPHONE®, SAMSUNG® device, GOOGLE® based mobile device, etc.), a tablet (e.g., APPLE® iPAD® or other like tablet device), a mobile computer or laptop, etc. In other embodiments, the method and system of the various embodiments can be accessed via a desktop computer, game console, or other computing system or device.

Accordingly, the mobile (or other) user device(s) 30 of the various embodiments of the present invention may include, among other components and devices structured to facilitate implementation of the present invention in the intended manner, a computer processor, memory, a data storage device, and communication or network device(s), a camera or image capturing device or module, a display screen, etc. Specifically, as used herein, the processor of at least one embodiment may include any device cooperatively structured to execute or implement computer instructions, software, etc., including, for example, the various features and components as described in accordance with at least one embodiment of the present invention and configured to implement or facilitate the implementation of the method herein. The data storage device, as used herein, may include a hard disk drive, USB drive, memory card, solid state drive, virtual drive, could-based storage drive, or other types of volatile or non-volatile memory. Further, the memory as used herein, may include but is not limited to random access memory (RAM) or other like devices configured to implement the present invention in the intended manner, for example, by storing and assisting with the execution of one or more applications, modules, or components capable of implementing the system and method described herein. It should be noted that non-transitory computer readable media includes all computer-readable media except for a transitory, propagating signal. Moreover, the communication device may include a network communication hardware/software component structured to facilitate communication between the mobile user device and a remote server, remote database or other remotely located computer system or device that may be used in connection with the operation of the present invention.

As will be described herein, in some embodiments, the user may want or need to take an image or photograph of herself or himself, such as his or her face. Accordingly, the mobile or other user device 30 may include one or more image capturing devices, such as a camera commonly found on consumer electronics and mobile phones.

Furthermore, the application 20 of the various embodiments of the present invention may be downloaded and installed on the mobile user device 30 or otherwise accessed via a web browser. Accordingly, some or all of the data associated with the present invention, may be stored on the mobile device itself, stored at a remote server or remote computer system and remotely accessed by the device 30 via the Internet or other computer-based network, or a combination of local storage (on the device) and remote storage (on a remote computer system).

Figure 2:
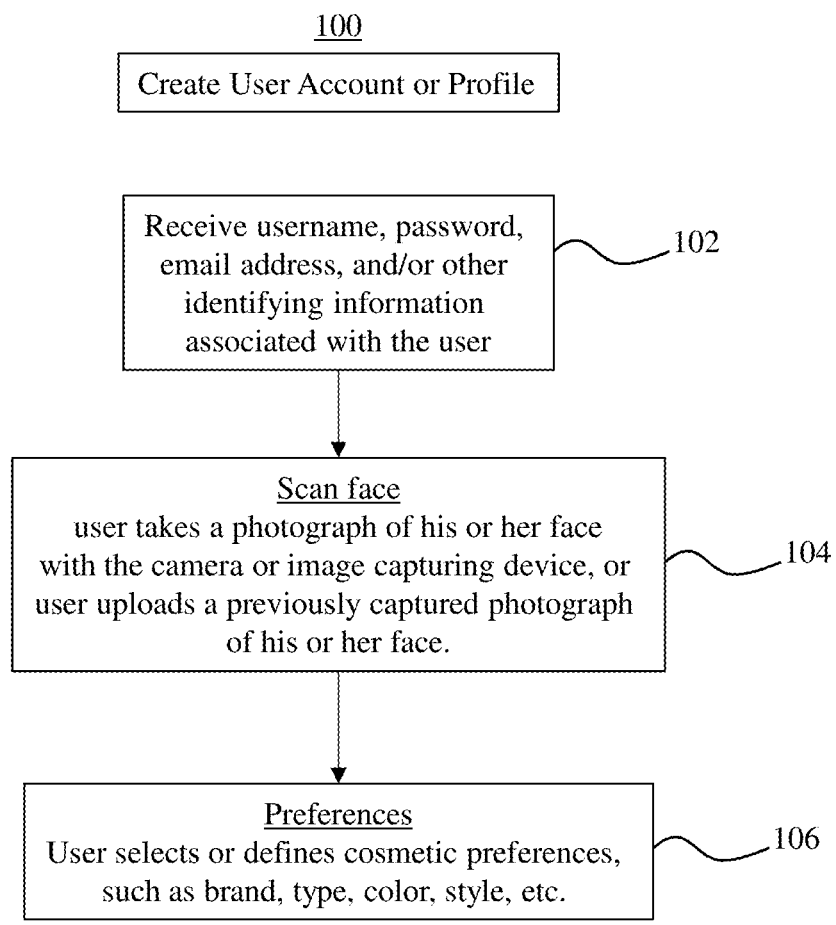
FIG. 2 is a high-level flow chart illustrating the creation of a user account and profile in accordance with at least one embodiment of the system and method disclosed herein.

In any event, and still referring to 100 in FIG. 1, FIG. 2, and the exemplary screenshots of FIGS. 7 and 8, the method 50 may begin with the creation of a user account or profile. In this manner, the user may enter some personal details or information, such as a username, password, and email address, as shown at 102 in FIG. 2 and as represented in FIGS. 7 and 8. This information will be used to create the user account or user profile, which, as above, may be stored locally and/or remotely. Other identifying information, such as the user's first name, last name, address, birth date, age, etc. may also be includes in the profile or account information in some embodiments.

Figure 9:
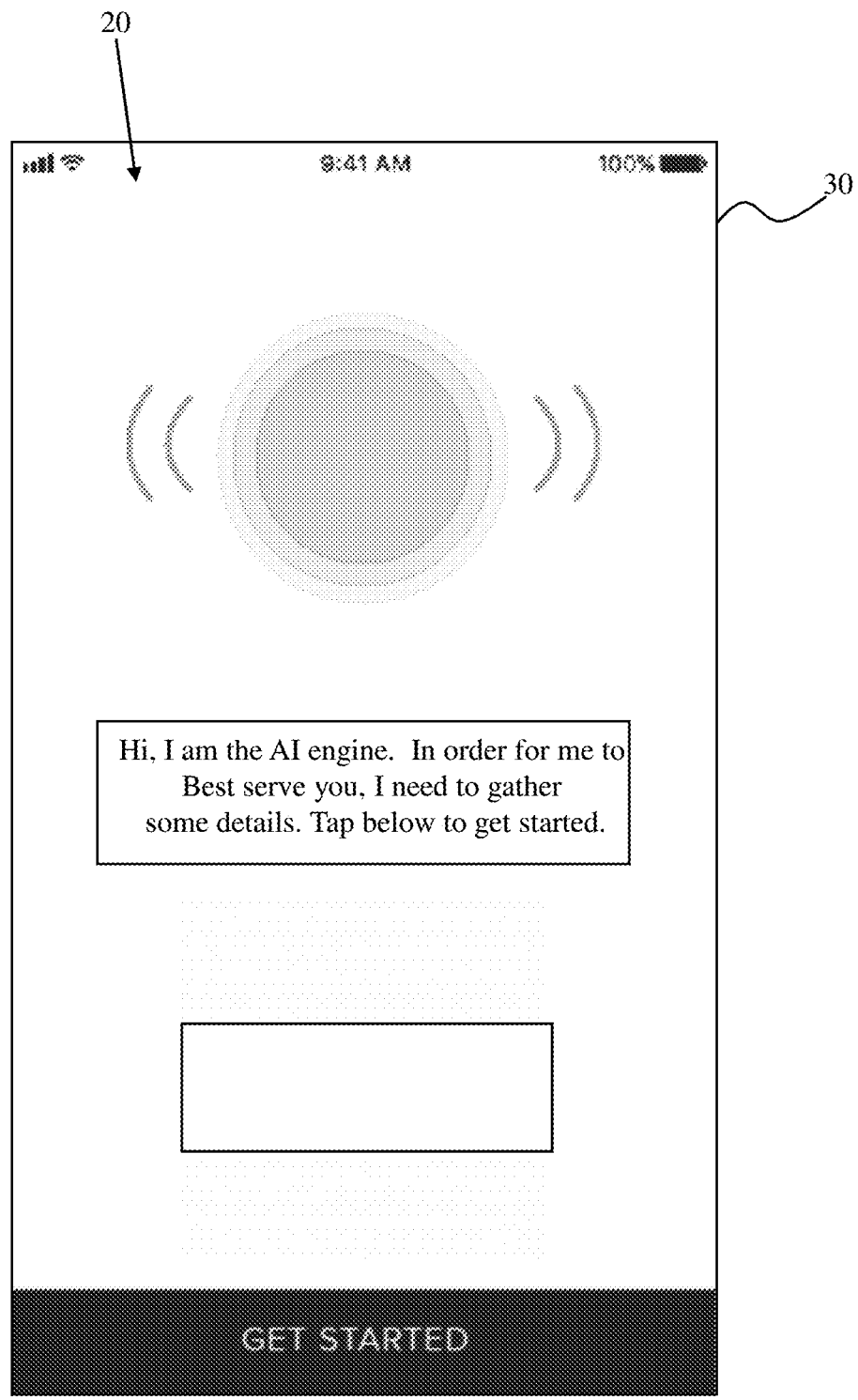
FIG. 9 is an exemplary screenshot of the application of at least one embodiment of the present invention illustrating an introduction to the AI engine (e.g., IBM Watson) as disclosed herein.
Figure 10:
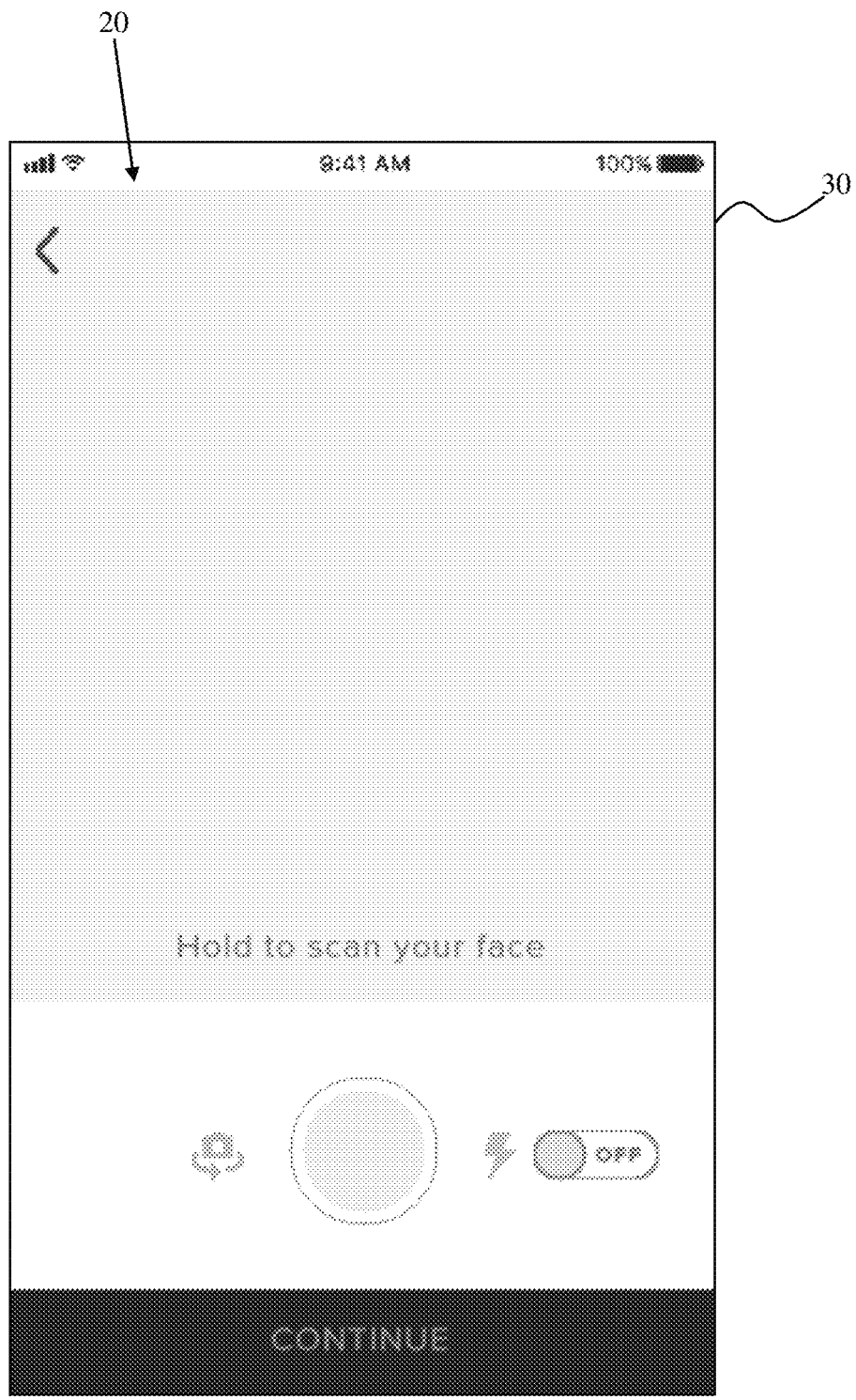
FIG. 10 is an exemplary screenshot of the application of at least one embodiment of the present invention illustrating an image capturing module for capturing a facial image of the user as disclosed herein.

As shown in FIG. 2 at 104, and in the exemplary screenshot of FIGS. 9 and 10, in at least one embodiment the user can scan his or her face or upload a previously captured photograph of his or her face. For example, using the camera or image capturing device of the mobile user device 30, the user may position the device and/or his or her face in a manner such that the device 20 will capture a clear, clean and head-on photograph of the user's face. The image can, and in most embodiments preferably does contain a picture of the front of the user's face capturing both eyes, the nose, mouth, and cheeks. As mentioned, the image may be a photograph that was previously captured, in which case, the user can select and upload a previous image, or in some case, the user can operate the application 20 of the present invention to capture an image from with the application 20, as represented in exemplary screenshot of FIG. 10.

This image or face photograph can be stored in the user's profile and can be used by the system, method and application as a historical image (e.g., for purposes of skin analysis), or for other features as disclosed and described herein.

Figure 11:
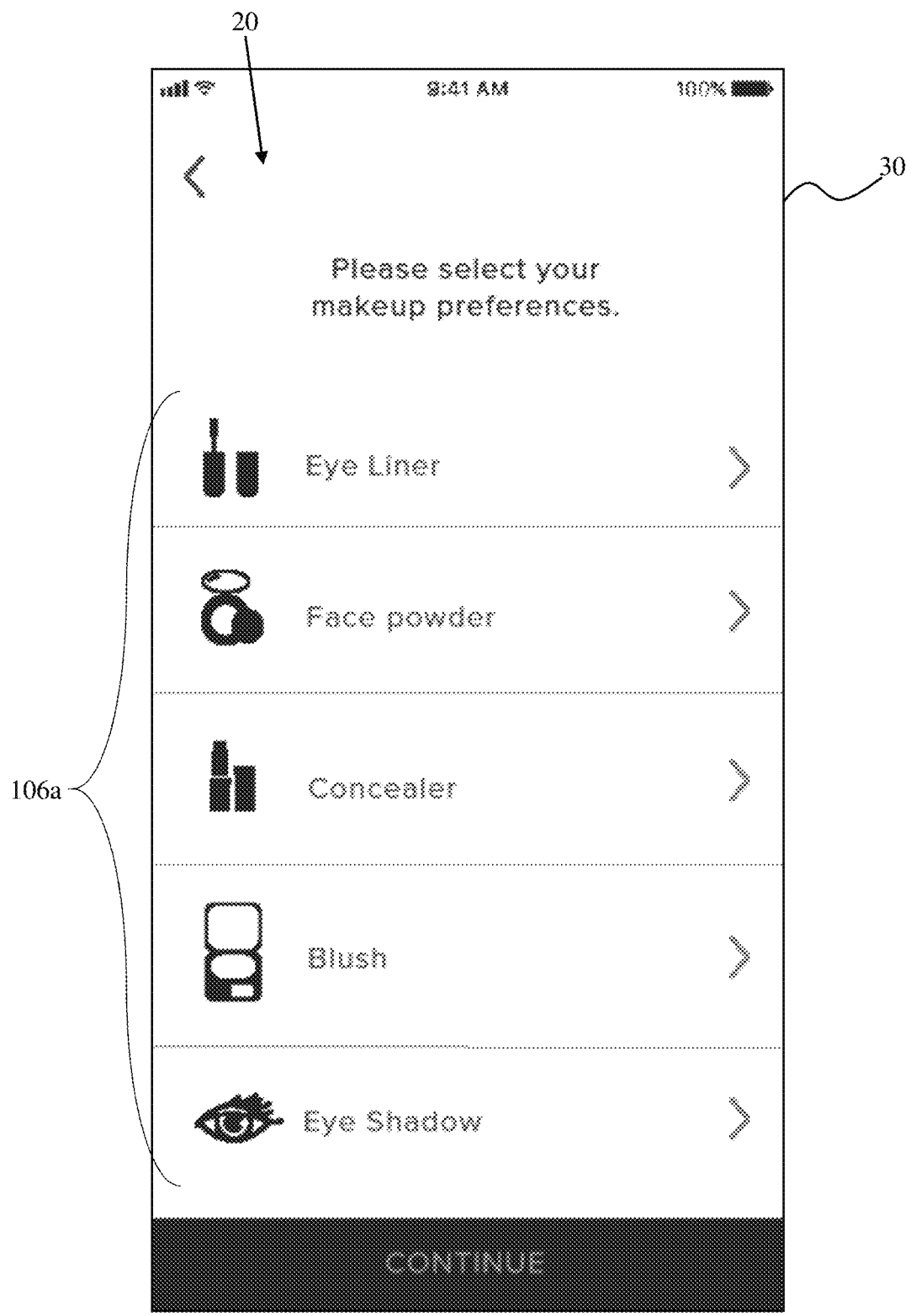
FIG. 11 is an exemplary screenshot of the application of at least one embodiment of the present invention illustrating a cosmetic preference selection module.
Figure 12:
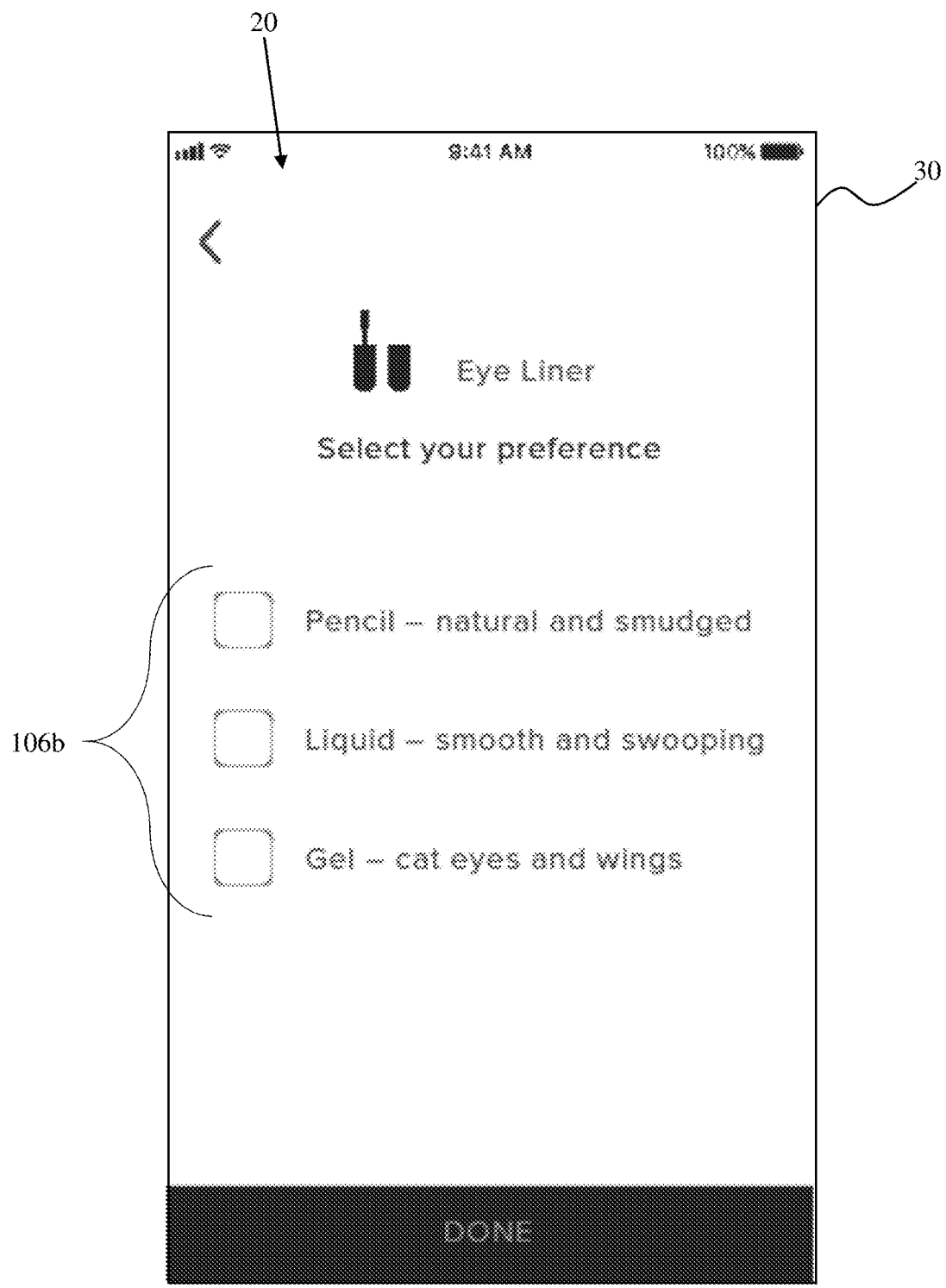
FIG. 12 is an exemplary screenshot of the application of at least one embodiment of the present invention illustrating a cosmetic preference selection module.

Furthermore, with reference now to 106 in FIG. 2 and the exemplary screenshot of FIG. 11, at least one embodiment of the present invention may further include receiving or gathering information from the user pertaining to preferences in cosmetics and other like products. For example, as shown in FIG. 11, the system, method and/or application of the present invention may display to the user, via the mobile (or other) user device 30 a list of a plurality of cosmetic categories 106a. In the example provided, the categories 106a may include "Eye Liner," "Face Powder," "Concealer," "Blush," and/or "Eye Shadow." The user can then select the categories 106a, one at a time, and define various preferences related to each category, some categories, one category, or none of the categories. Specifically, when a user selects one of the categories 106a, additional details or sub-categories 106b (shown in FIG. 12) may be displayed. As just an example, with regard to the "Eye Liner" category, additional sub-categories may be included, such as "Pencil," "Liquid" or "Gel."

In this manner, the user can select or define what eye liner he or she prefers to use. This information can then be stored in connection with or in association with the corresponding user's profile or account. The user preferences can then be used by the system, method and application of at least one embodiment in order to recommend products or to provide cosmetic recommendations and instructions, as described in accordance with at least one embodiment herein.

Next, and referring back to FIG. 1, the present invention may also include the creation of a baseline facial model for the user, represented as 200. In particular, the baseline facial model of at least one embodiment of the present invention may include a model, representation or a combination of data, instructions, preferences, and images, that represent the user's "ideal" cosmetic application or otherwise represents the user's desired application of cosmetics to his or her face. Specifically, the baseline facial model may be a photograph or image 210 of the user when the user's make-up or cosmetic application is or was "ideal" according to the user. In other embodiments, the baseline facial model may include a combination of the user's "ideal" photograph or image 210 and one or more other selections or preferences, as described herein, and as represented in FIGS. 3, 13, and 14.

Figure 13:
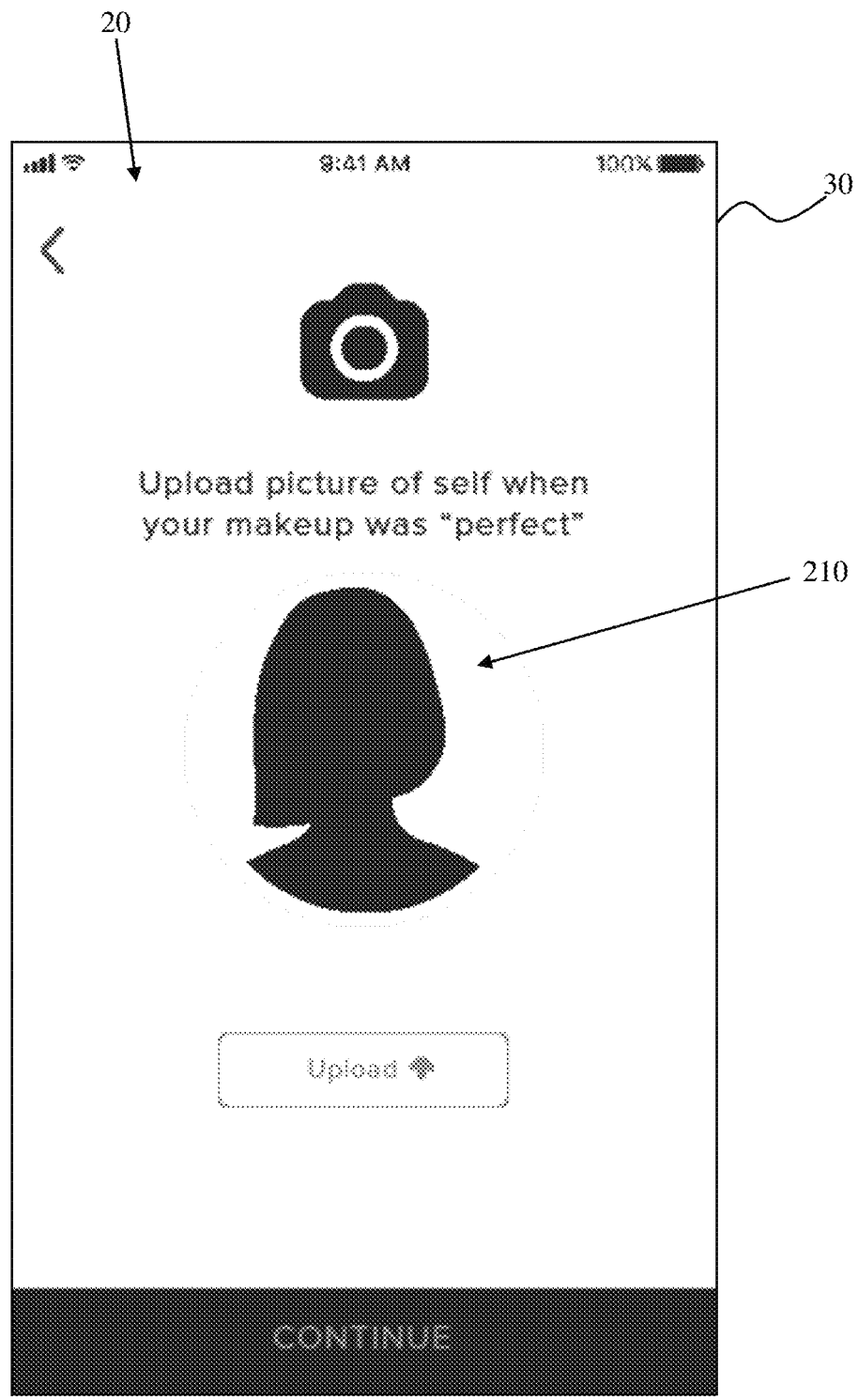
FIG. 13 is an exemplary screenshot of the application of at least one embodiment of the present invention illustrating an image capturing module for the user to upload an "ideal" self-image as disclosed herein.
Figure 14:
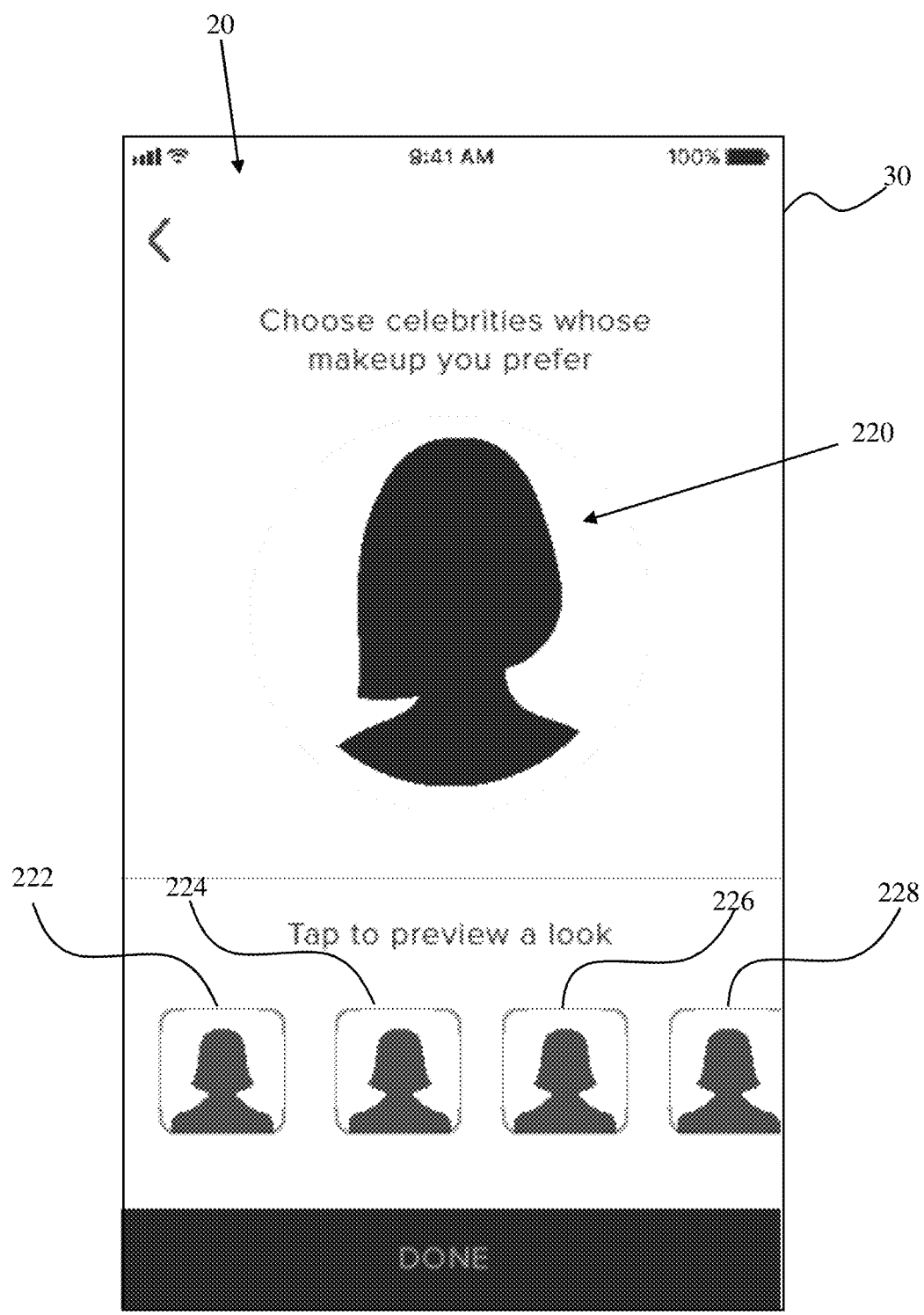
FIG. 14 is an exemplary screenshot of the application of at least one embodiment of the present invention illustrating a plurality of models or celebrities from which the user can select, as disclosed herein.

For instance, referring to FIGS. 2 and 13, and as described above, creation of the baseline facial model includes uploading or capturing an image or photograph 202, 210 of the user's face with make-up or cosmetics applied. Preferably, the photograph 210 is a clear head shot of the user showing the front of the user's face. This can help the system, method and application, understand the type of look the user is attempting to achieve.

In addition, creating the baseline facial model 200 may also include selecting one or more images or photographs of other people, models, or celebrities with different make-up or cosmetic applications. For example, as shown in FIG. 3 (204) and in FIG. 14, the system, method and application of at least one embodiment may present to the user or to the mobile user device a plurality of model images 220, 222, 224, 226, 228 each of which represent different applications of cosmetics to a model's face. Specifically, there may be one model with different make-up or cosmetic applications, or a plurality of models with different make-up or cosmetic applications. The models may be famous, generally known or recognizable, or generally unknown models.

In any event, the user may select one more model images 220, 222, 224, 226, 228 representing the desired look or cosmetic application of which he or she is attempting to achieve. The system, method and application, for example, an artificial intelligence (AI) engine incorporated therein or in communication therewith, may then analyze or process the user's uploaded baseline image 210 and the user's selection(s) of model images to create or define the baseline facial model, as represented as 200 in FIG. 3. The baseline facial model, which comprises a plurality or combination of data, techniques, images, and artificial intelligence, can then be saved to the user's profile or account 206 for subsequent retrieval and processing.

Figure 15:
FIG. 15 is an exemplary screenshot of the application of at least one embodiment of the present invention illustrating another cosmetic preference selection module.

With reference to FIG. 15, in some embodiments, the system, method and application may obtain a selection or selections from the user as to what makeup products or cosmetic products the user prefers to use. This may be a brand of cosmetics, or categories of cosmetics. The selection may be used by the AI to create different baseline images or models of the user.

For example, the AI engine of at least one embodiment of the present invention can generate different images or photos of the user based upon the uploaded or captured photograph 210, the model selection 220, 222, 224, 226, 228, and in some cases, other information such as preferences identified to the system by the user. The user can then choose the one image of himself or herself generated by the AI engine that mostly resembles the user's ideal self, or otherwise most closely resembles the look in which he or she is attempting to achieve. This selection will then be defined as the baseline facial model for use by the system, method, application or AI engine thereof, as described herein.

Figure 4:
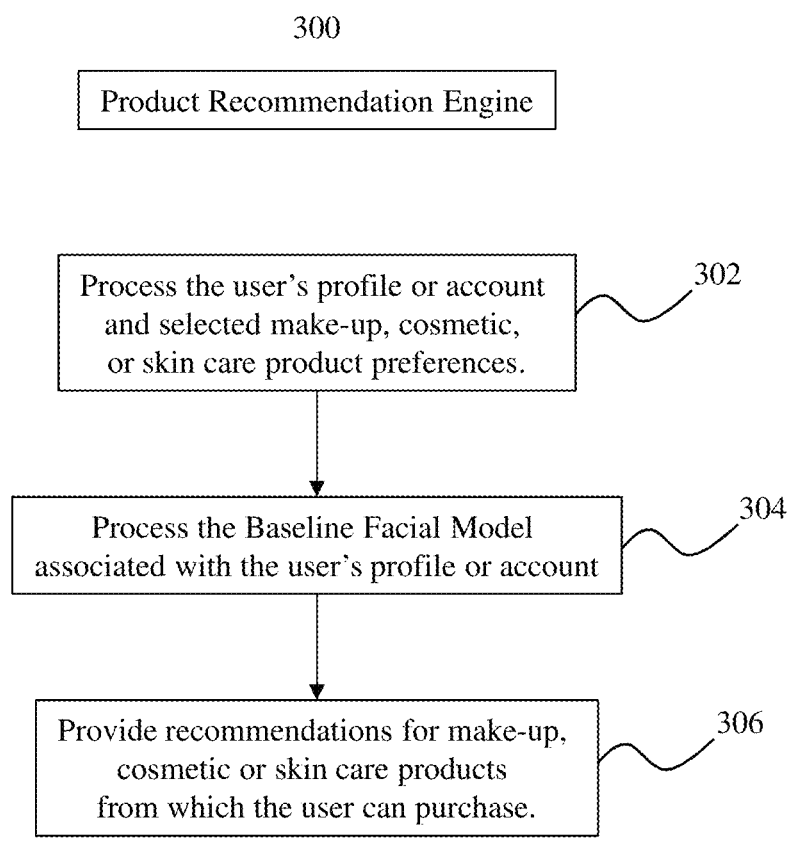
FIG. 4 is a high-level flow chart illustrating the product recommendation engine in accordance with at least one embodiment of the system and method disclosed herein.
Figure 16:
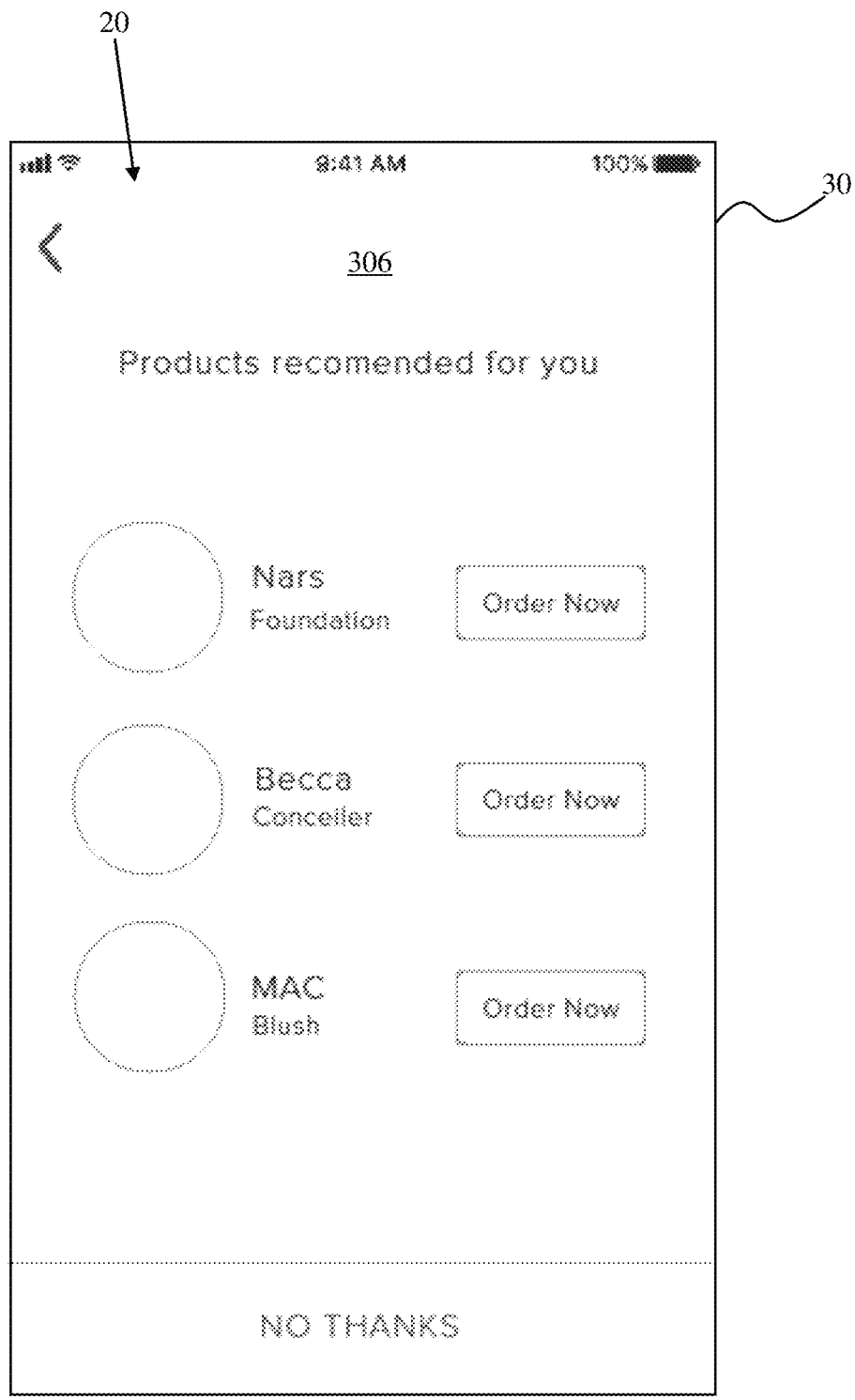
FIG. 16 is an exemplary screenshot of the application of at least one embodiment of the present invention illustrating a product recommendation engine as disclosed herein.

With reference to 300 in FIGS. 1, 4 and 16, at least one embodiment of the present invention further includes a product recommendation engine structured to provide recommendations to the user as to which products he or she may want to purchase and use. For example, as shown in the flow chart of FIG. 4, the recommendation engine may process or analyze the user's profile 302, such as one or more preferences provided by the user, as described above. Particularly, the user's profile or account may include an identification of preferred cosmetics, in the form of a preferred category, sub-category, style, types, color, shade, or brand. In addition, in some embodiment, the recommendation engine may also process or analyze the user's baseline facial model 304 to determine what cosmetics may be included in the ideal self-image or model. For example, the AI engine or recommendation engine may determine that the user prefers a particular type or color of eye shadow or eye liner based upon the preferences and/or the baseline facial model.

In any event, with reference to FIG. 16, at least one embodiment of the system, method and application may present product recommendations 306 to the user or to the mobile user device. Those product recommendations may, in some cases, be purchased by the user within the application for example by selecting an "Order Now" or similar button or link. Although in other embodiments, the user may be directed to an external website or application to complete the purchase.

Figure 17:
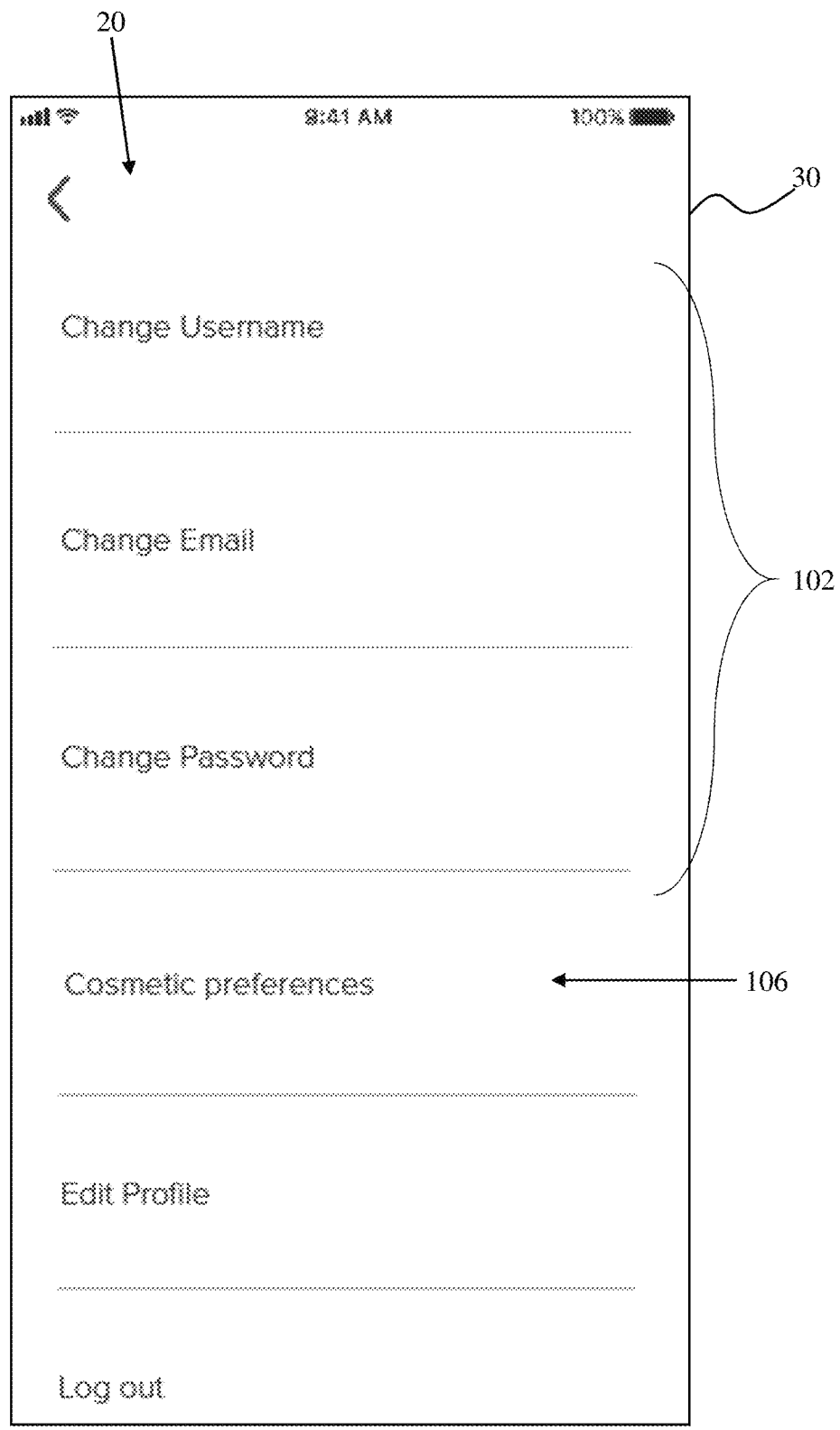
FIG. 17 is an exemplary screenshot of the application of at least one embodiment of the present invention illustrating a user profile menu within which a user can change user preferences.

FIG. 17 represents an exemplary screenshot that allows the user to change various information or data associated with his or her profile or account. For example, the user is able to change cosmetic preferences, represented as 106, at any time, including changing preferred brands, types of make-up, categories 106a, sub-categories, colors, consistencies, etc. Other changes can be made to the username, email, or password, shown at 102, or other details of the profile or account.

Figure 18:
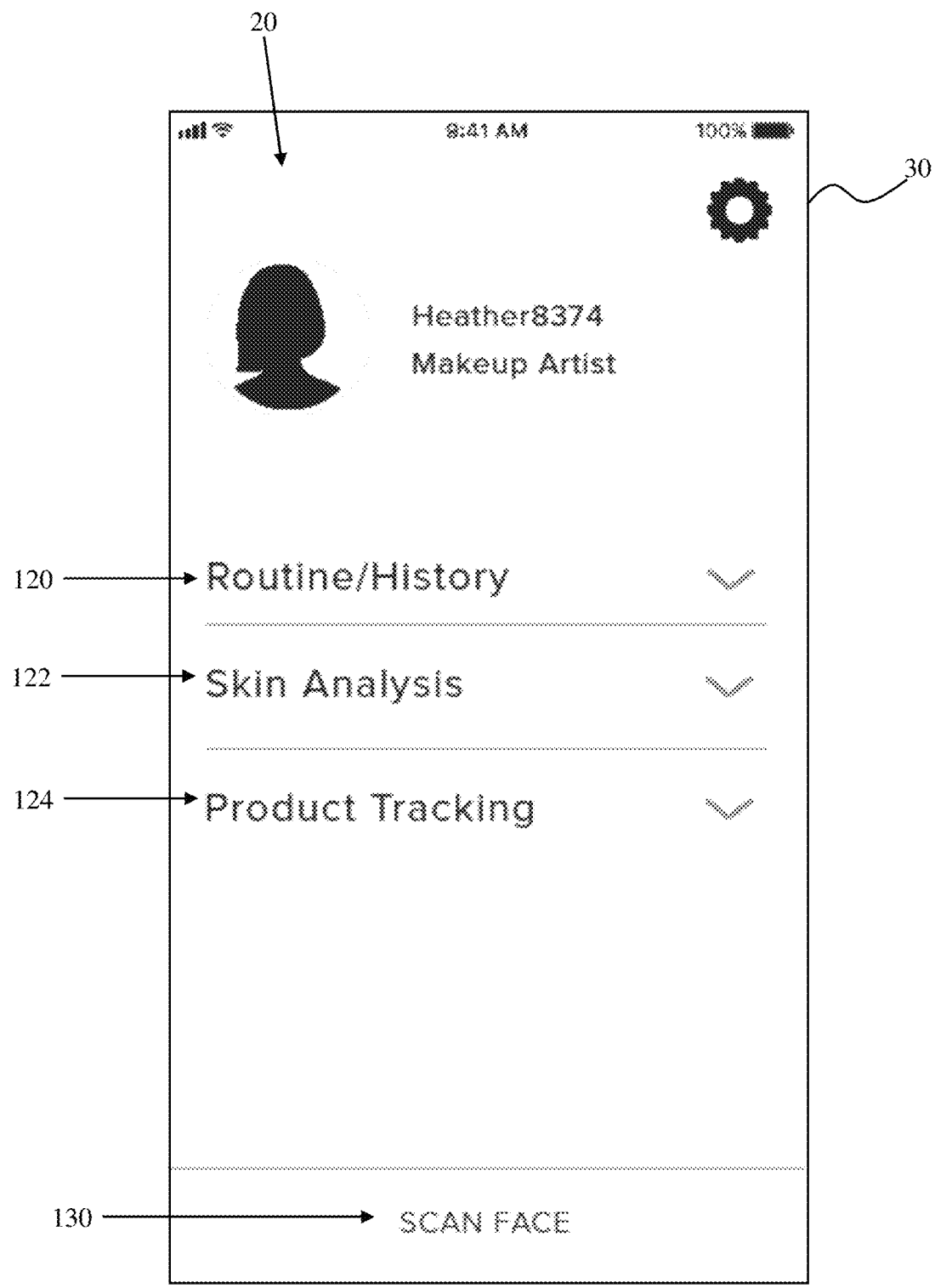
FIG. 18 is an exemplary screenshot of the application of at least one embodiment of the present invention illustrating a user menu providing a plurality of options available within the application, including, for example, review of routine history, access to the skin analysis engine, access to a product tracking screen, and access to the cosmetic analysis engine.

With reference now to FIG. 18, an exemplary screenshot is shown that provides a menu to the user for selecting certain functions and capabilities of the system, method and application of the present invention. For example, the application may include a "Routine/History" tab or selection 120, a "Skin Analysis" tab or selection 122, and a "Product Tracking" tab or selection 124. Other tabs, selection, sections or features may be included within the full spirit and scope of the present invention.

Figure 19:
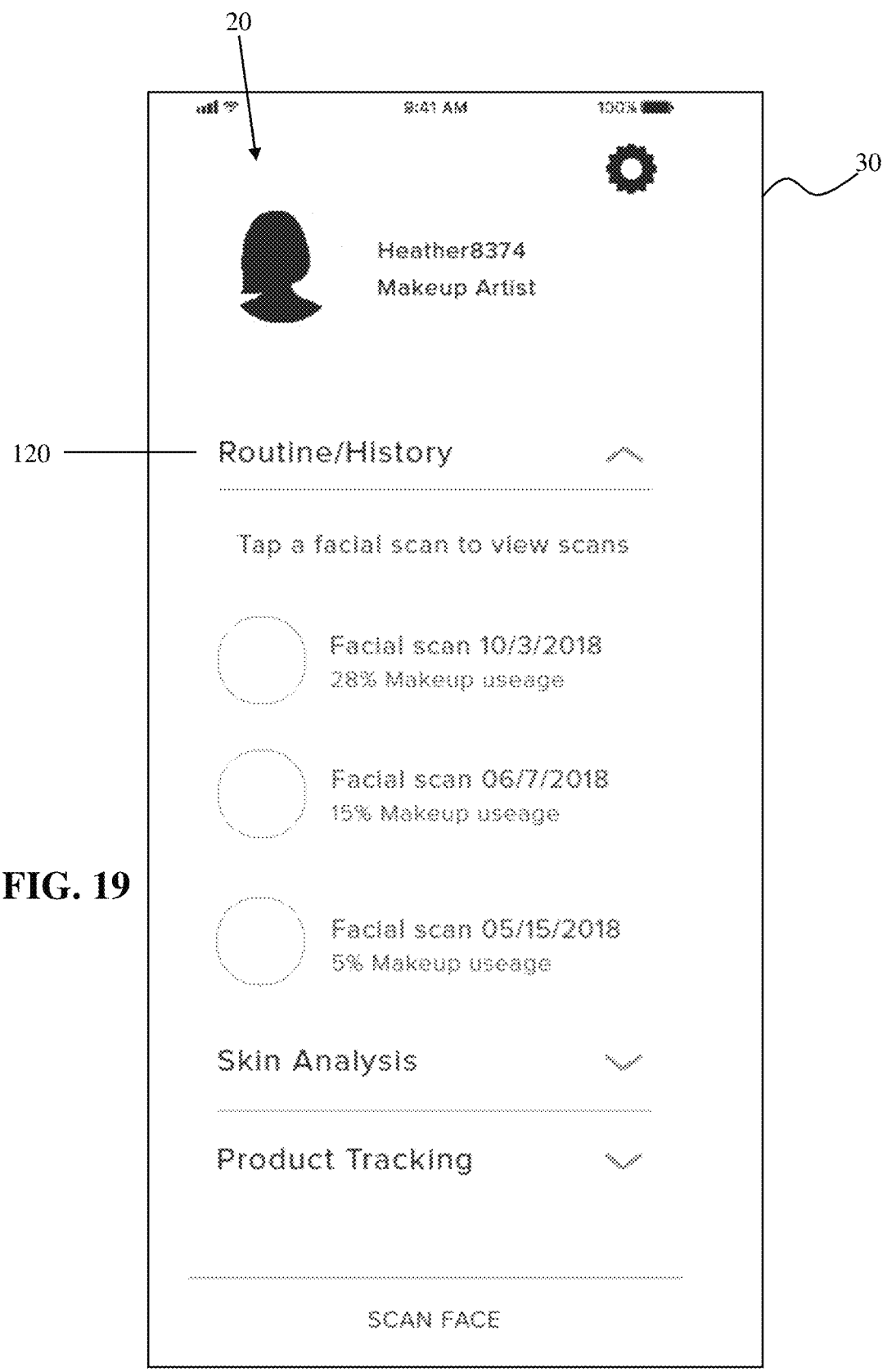
FIG. 19 is an exemplary screenshot of the application of at least one embodiment of the present invention illustrating an exemplary routine or history list.

FIG. 19 illustrates an exemplary screenshot when the "Routine/History" tab 120 is selected. For instance, at least one embodiment of the present invention is structured to store facial scans or images uploaded by the user. This will create a historical library of images of the user's face over time. In the example of FIG. 19, there are three (3) historical images available—one that was uploaded on Oct. 3, 2018, one that was uploaded on Jun. 7, 2018 and one that was uploaded on May 15, 2018. The user is able to select and view the historical images, if and when desired by clicking on the corresponding labels. In addition, and still referring to FIG. 19, the AI engine or method of the present invention may be configured to determine a percentage of make-up that is applied in the image, for example, as compared the baseline facial model. In this regard, the exemplary facial scan of Oct. 3, 2018 has an estimated 28% of makeup used.

Figure 20:
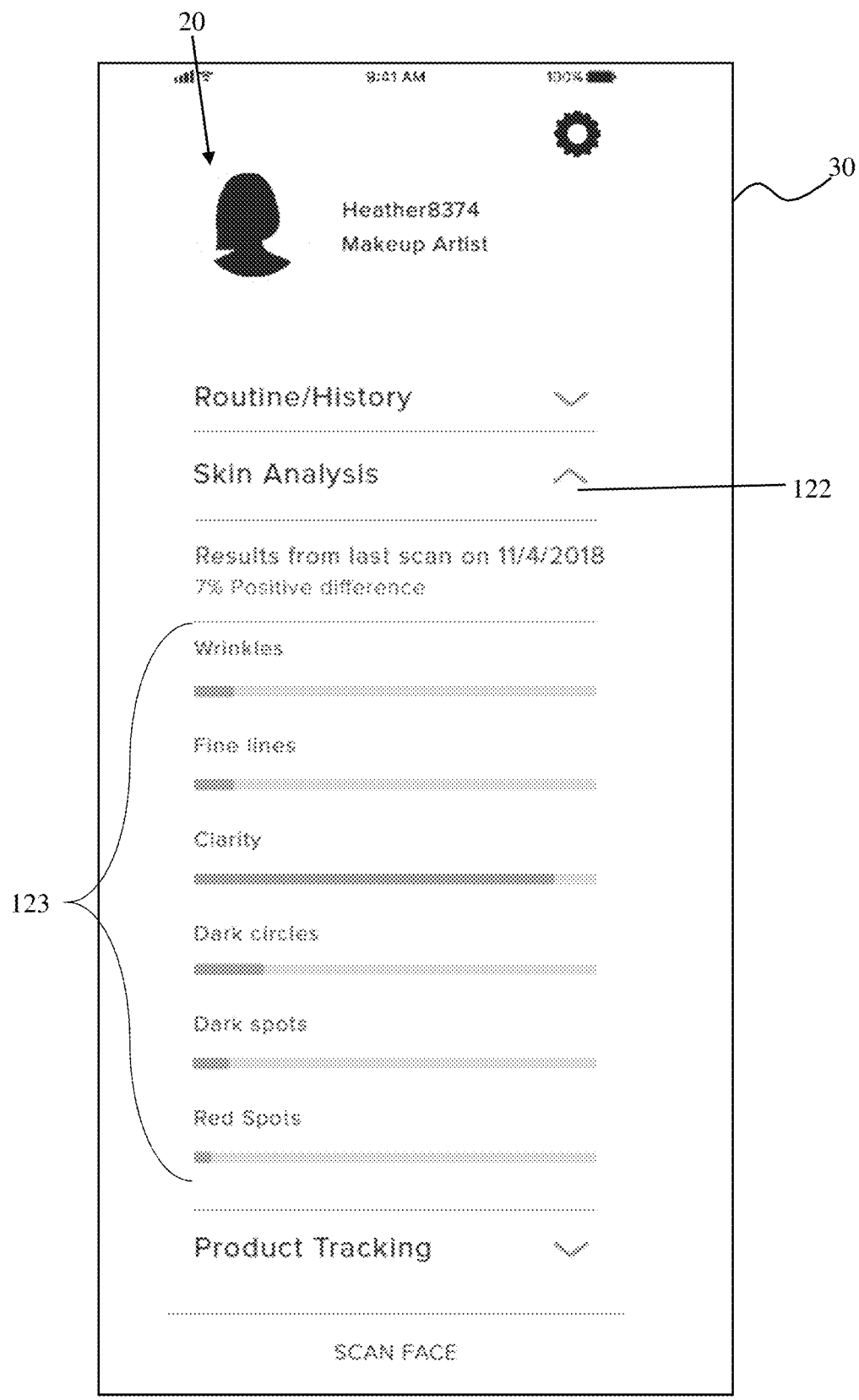
FIG. 20 is an exemplary screenshot of the application of at least one embodiment of the present invention illustrating a report generated by the skin analysis engine as disclosed herein.

With reference now to FIG. 20, an exemplary screenshot is provided illustrating when the "Skin Analysis" tab 122 is selected. Particularly, at least one embodiment of the present invention includes a skin analysis engine, represented as 400 in FIG. 5, which is configured to analyze the historical facial images or scans and to identify one or more skin properties on the user's face. Specifically, the skin analysis engine is configured to provide a history of changes of the user's skin over time. This can be important to those users who want to track changes in their skin, such as changes in any wrinkles, fine lines, clarity, circles, dark bags under the eyes, dark spots, red sports, pores, etc. The skin analysis engine can be used to track the user's skin age and health, and can be used to help understand whether skin-care products are working or if a particular skin-care routine is effective. For instance, the skin analysis engine of at least one embodiment may spot changes occurring on the user's skin, whether for the positive or negative.

In particular, the system, method and application of the present invention may receive, over time, a plurality of images of the user's face—e.g., whether uploaded into the application, or captured by the camera and image capturing capabilities of the application and mobile user device. As shown at 404 in FIG. 5, the historical images are then processed by the skin analysis engine in order to identify one or more skin properties, such as, but not limited to, coloration, wrinkles, spots, fine lines, clarity, circles, dark bags under the eyes, dark spots, red sports, pores, etc. In some embodiments, the user may decide to create or upload a current image or photograph of his or her face, as represented at 402. In this case, the skin analysis engine may also analyze the current image along with the historical images in much the same way.

In any event, the various images, e.g., historical images and/or current image, are then compared to one another in order to determine a change of at least one of the properties 404. For example, whether the wrinkles have grown and become more plentiful, or whether they have gotten smaller or fewer in number.

Figure 5:
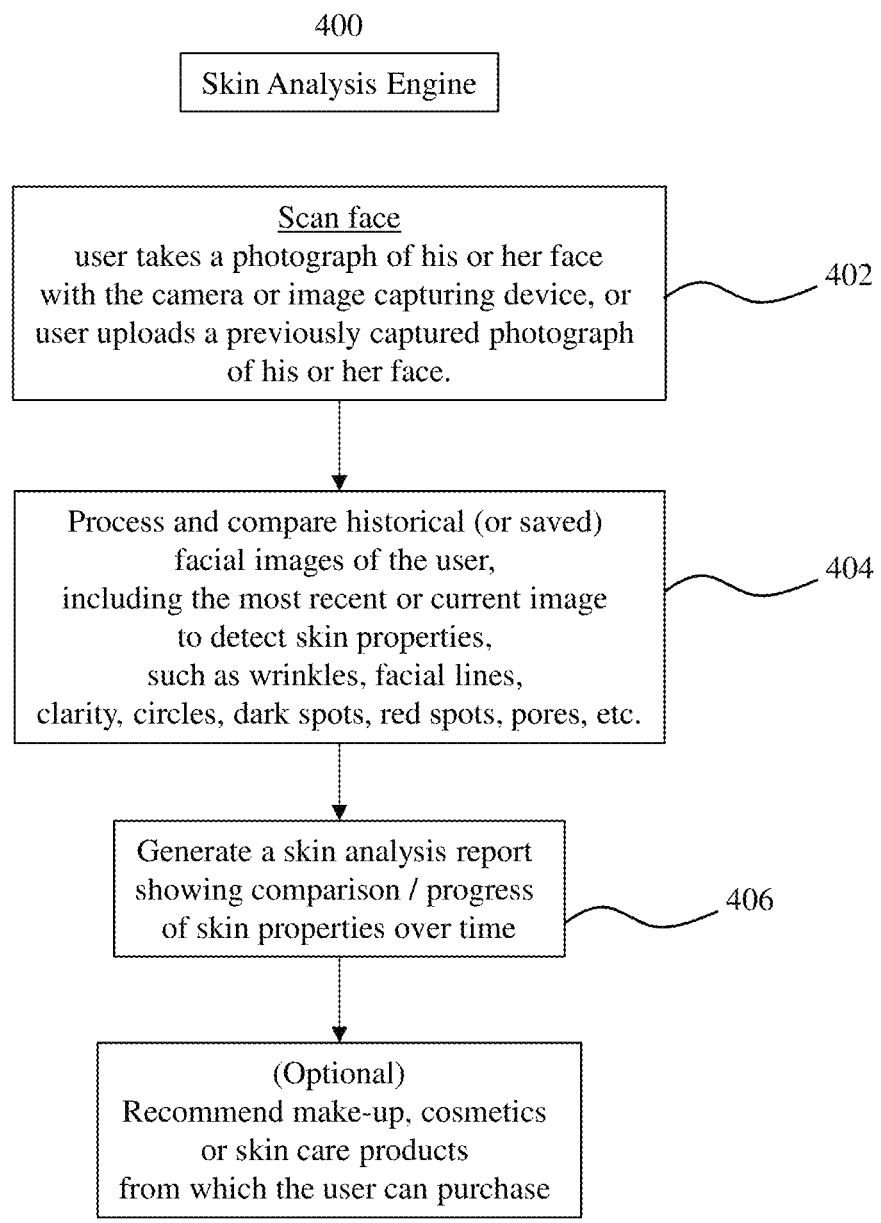
FIG. 5 is a high-level flow chart illustrating the skin analysis engine in accordance with at least one embodiment of the system and method disclosed herein.

Based on the comparison or processing of the images, as shown at 406 in FIG. 5 and at 123 in FIG. 20, the system, method and application will generate a skin analysis report. The report 123 may include an identification of one or more properties of the skin or face which were recognized by or processed by the skin analysis engine. This may include, for example, wrinkles, fine lines, clarity, dark circles, dark spots, and red spots, as shown in FIG. 20, although other skin properties may be included as well. For each of the properties, the report 123 will indicate whether the property has gotten worse over time, better over time, or otherwise provide a graph showing the strength of each of the properties.

With reference to FIG. 5, the system, method and application of at least one embodiment can also (and optionally) recommend products to the user, for example, products which may help with any one or more of the skin properties identified by the skin analysis engine.

Figure 21:
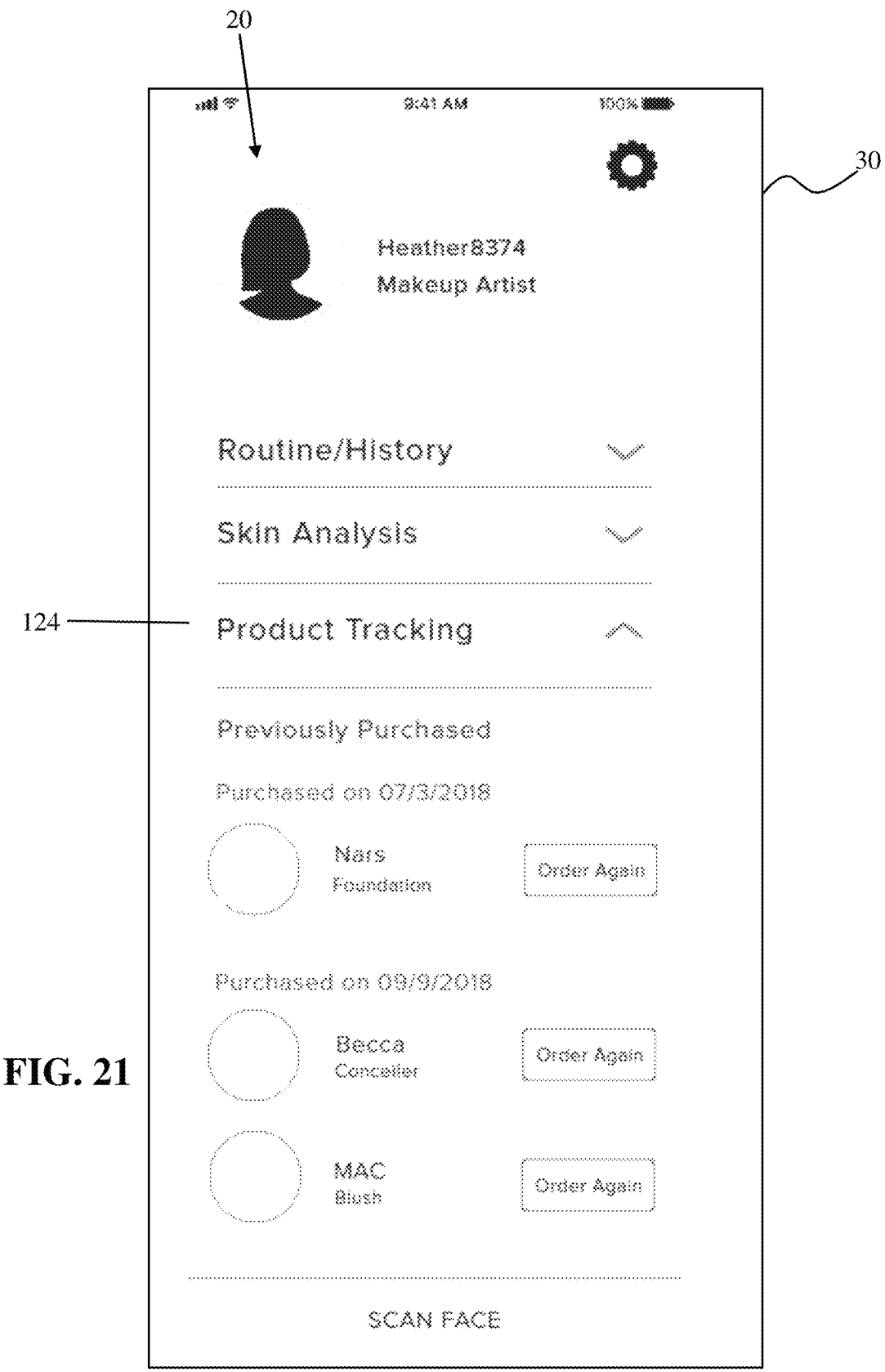
FIG. 21 is an exemplary screenshot of the application of at least one embodiment of the present invention illustrating a report generated by the product tracking module.

Referring now to FIG. 21 an exemplary screenshot is illustrated when the "Product Tracking" tab is selected. This tab can be used to view previously purchased cosmetics or skin care products, and thus, allows the user to easily view which products have been purchased or ordered in the past. Refills or new orders are thus easily obtained.

Figure 6:
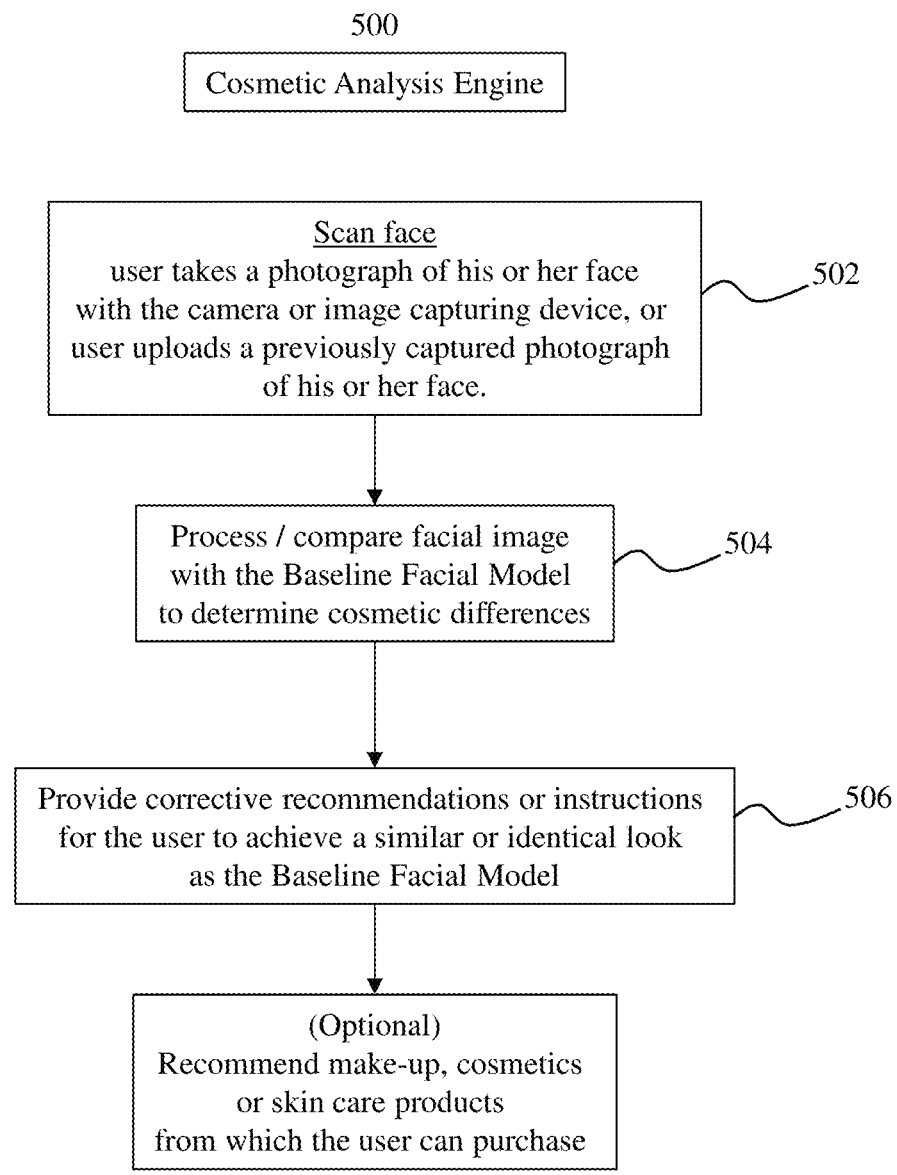
FIG. 6 is a high-level flow chart illustrating the cosmetic analysis engine in accordance with at least one embodiment of the system and method disclosed herein.
Figure 22:
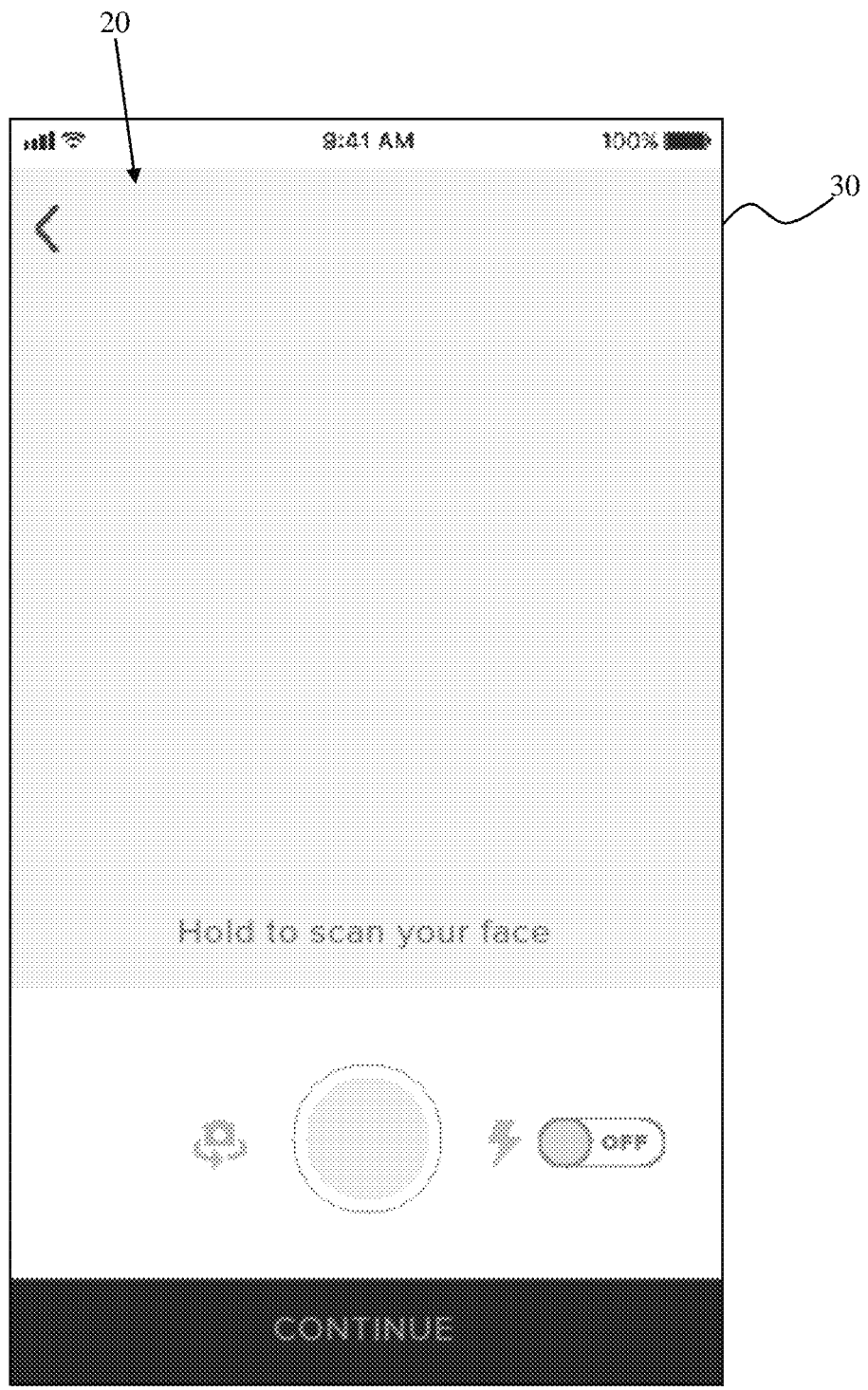
FIG. 22 is an exemplary screenshot of the application of at least one embodiment of the present invention illustrating an image capturing module form which the user can capture a facial image.
Figure 23:
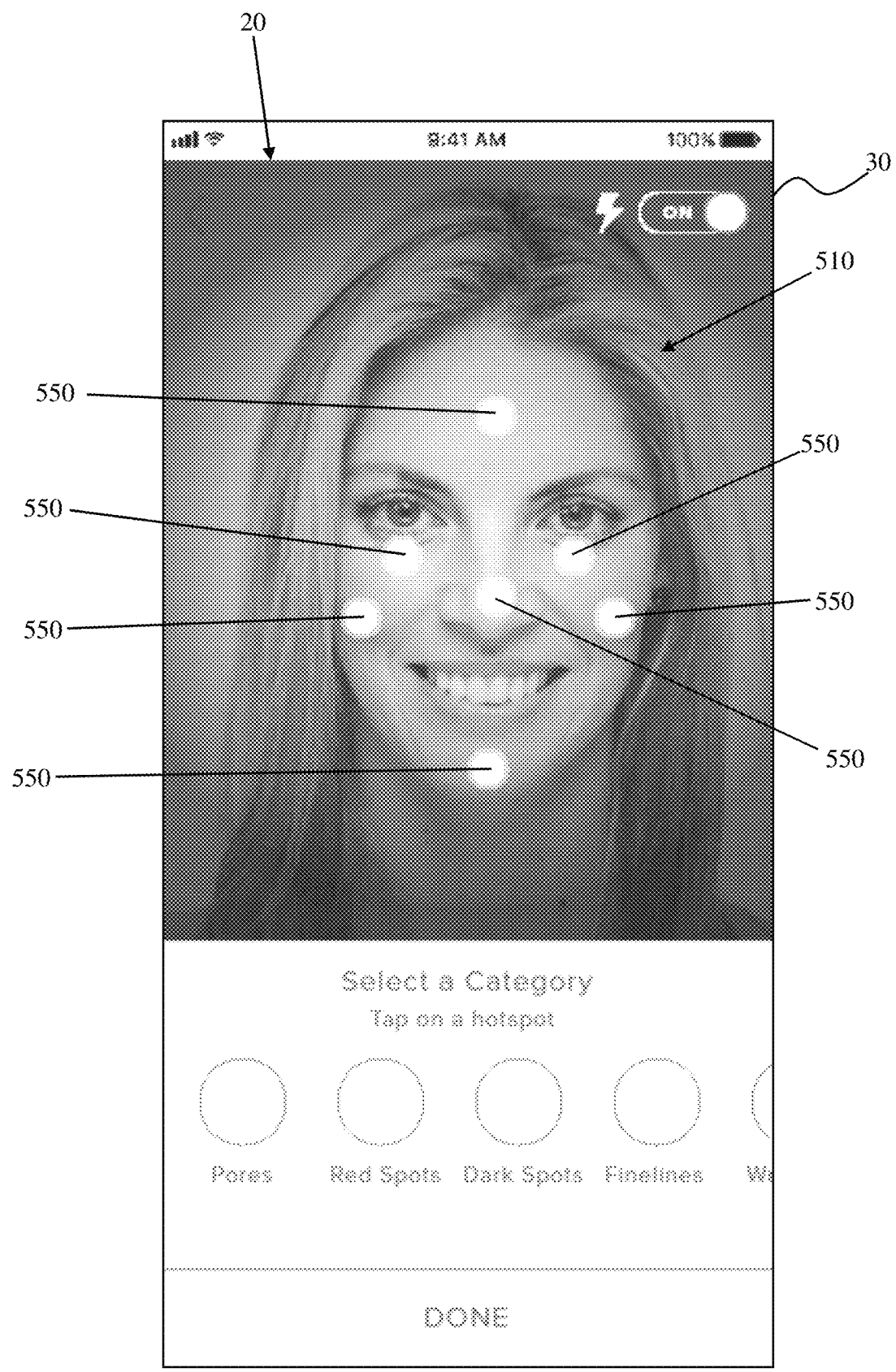
FIG. 23 is an exemplary screenshot of the application of at least one embodiment of the present invention illustrating an exemplary report and analysis generated by the cosmetic analysis engine as disclosed herein.
Figure 24:
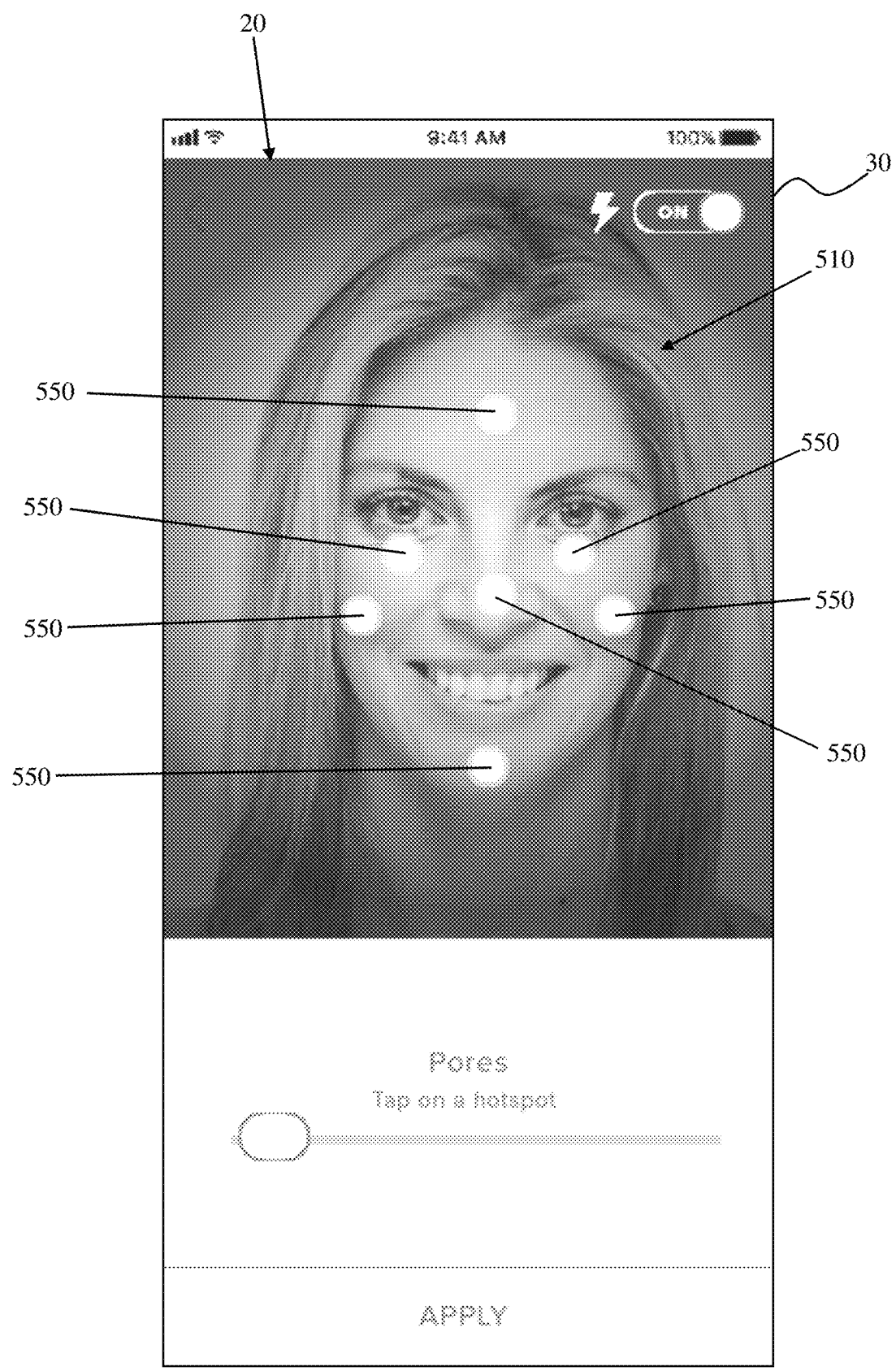
FIG. 24 is another exemplary screenshot of the application of at least one embodiment of the present invention illustrating an exemplary report and analysis generated by the cosmetic analysis engine as disclosed herein.

With reference now to FIG. 1, numeral 500, the flow chart of FIG. 6 and the screenshots of FIGS. 22 through 24, the present invention further includes a cosmetic analysis engine. Particularly, the cosmetic analysis engine 500 is structured to receive a facial image or photograph of the user's face 502, compare the image of the user's face with the baseline facial model associated with the user's profile or account 504, and providing corrective cosmetic instructions or recommendations to the user or mobile user device 506.

For example, FIG. 22 represents a screenshot where a user can scan his or her face using the application 20 of at least one embodiment of the present invention. As an example, the user can select the "Scan Face" option shown in FIG. 18, to open the image capturing capabilities of the application 20. Doing so, will allow the application 20 and the camera of the mobile user device to capture an image, preferably a head on or straight on shot of the user's face. Particularly, the image may preferably include a clear photograph of the user's eyes, nose, forehead, and cheeks (see FIGS. 23 and 24 for example). It should also be noted however, in other embodiments, the user may upload a photograph previously taken, for example, a photograph in the camera roll of the mobile device or stored at another location.

In any event, the cosmetic analysis engine of the present invention is structured to receive the image of the user's face and compare that image to the baseline facial model associated with the user's profile. As discussed above, the baseline facial model is a representation or model of the user's face created by the AI engine that represents the ideal application of cosmetics to the user's face, including the type of cosmetic, color(s) of cosmetics, techniques (e.g., blending) of cosmetics, etc.

After the AI engine or cosmetic analysis engine compares the current image of the user's face with the previously generated baseline facial model, corrective recommendations are provided to the user, via the mobile user device 30. Specifically, the corrective cosmetic recommendations generated by the cosmetic analysis engine 500 may include displaying at least one overlay upon the image of the user's face in a location that corresponds with a recommendation. As an example, with reference to FIG. 23, a plurality of overlays or hotspots 550 are displayed on top of or otherwise along with the image 510 of the user's face. The overlays 550 are positioned on the face or image 510 that corresponds with a particular recommendation. In other words, each of the overlays 550 represents a recommendation, instruction or comment with regard to the comparative analysis between the image 510 and the baseline facial model previously created.

The corrective recommendation may be an instruction to apply a particular cosmetic (e.g., eye liners, blush, eye shadow) to a particular location, an instruction to apply more of a cosmetic to a particular location, an instruction to apply a particular technique (blending) to a particular location of the face, etc. The user may tap on or select one of the overlays or hotspots to reveal the corresponding cosmetic recommendation.

Additionally, in at least one embodiment, the system, method and application may virtually apply one or more cosmetics, cosmetic techniques or cosmetic recommendations to the image, allowing the user to virtually visualize the changes without actual application to his or her face. For instance, with reference to FIGS. 23 and 24, the user may select a listed category (e.g., pores, red spots, dark spots, fine lines, wrinkles, etc.), and apply recommended changes or other desired changes to the user's image. After selecting a category, the user can then select one or more of the overlays or hotspots to make the particular changes, virtually. If the user likes the changes or recommendations, he or she can then apply the modifications, cosmetics or techniques to his or her face in real life.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. This written description provides an illustrative explanation and/or account of the present invention. It may be possible to deliver equivalent benefits using variations of the specific embodiments, without departing from the inventive concept. This description and these drawings, therefore, are to be regarded as illustrative and not restrictive.

Now that the invention has been described,

What is claimed is:

1. A method for cosmetic analysis, the method comprising:

creating a baseline model for a user, the baseline model being representative of the user's desired application of cosmetics, wherein creating the baseline model for the user comprises:

receiving, from a mobile user device, a baseline image of at least a portion of the user's face, the baseline image representing the user's desired application of cosmetics to the user's face, presenting, to the mobile user device, a plurality of model images, each of the plurality of model images representing different applications of cosmetics to at least one model face, receiving, from the mobile user device, a selection of at least one of the plurality of model images representing a desired application of cosmetics to the model face, processing the baseline image for cosmetic application to the user's face shown therein, processing the selected one of the plurality of model images for cosmetic application to the model face shown therein, creating the baseline model using at least the determined cosmetic application to the user's face shown in the baseline image and the determined cosmetic application to the selected one of the plurality of model images, saving the baseline model to a profile associated with the user, and providing cosmetic instructions to the user, comprising:

receiving, from the mobile user device, a comparison image of at least a portion of the user's face, processing the comparison image and comparing the comparison image to the baseline model associated with the user's profile, defining at least one corrective cosmetic recommendation based upon any differences identified when comparing the comparison image to the baseline model, and displaying at least one overlay upon the comparison image in a location corresponding to the at least one corrective cosmetic recommendation.

2. The method as recited in claim 1 further comprising defining the at least one corrective cosmetic recommendation as comprising an instruction to apply an identified cosmetic to an identified portion of the user's face represented on the comparison image.

3. The method as recited in claim 1 further comprising defining the at least one corrective cosmetic recommendation as comprising an instruction to apply a cosmetic technique to an identified portion of the user's face represented on the comparison image.

4. The method as recited in claim 1 further comprising providing a cosmetic product recommendation comprising an identification of a cosmetic product.

5. The method as recited in claim 4 wherein the cosmetic product recommendation is based at least in part upon the processing of the comparison image with the baseline model.

6. The method as recited in claim 4 wherein the cosmetic product recommendation is based at least in part upon a selected preferred cosmetic associated with the user's profile.

7. The method as recited in claim 1 further comprising processing a plurality of images of the user's face and providing a skin analysis based there upon.

8. The method as recited in claim 7 wherein the plurality of images of the user's face comprises at least one historical image.

9. The method as recited in claim 8 wherein processing the plurality of images the user's face comprises identifying, on at least one of the plurality of images of the user's face, a property of the user's skin, and identifying a change of the property of the user's skin in another one of the plurality of historical images.

10. The method as recited in claim 9 further comprising defining the property of the user's skin as comprising a wrinkle.

11. The method as recited in claim 9 further comprising defining the property of the user's skin as comprising at least one of a wrinkle, a line, a circle, a spot or a pore.

12. A method for providing a skin analysis and a cosmetic analysis, the method comprising:
defining the skin analysis as comprising:
receiving, over time, from a mobile user device, a plurality of images of a user's face and storing the plurality of images of the user's face with a profile associated with the user,
processing the plurality of images of the user's face to identify at least one property of the user's skin,
comparing the plurality of images of the user's face to determine a change of the at least one identified property of the user's skin between the plurality of images of the user's face, and
creating a skin analysis report of the user's face, the skin analysis comprising an identification of the at least one property of the user's skin and an identification of a determined change of the at least one property over time based upon the comparison of the plurality of images of the user's face,
defining the cosmetic analysis as comprising:
creating a baseline model for the user, the baseline model being representative of the user's desired application of cosmetics,
receiving, from the mobile user device, a comparison image of at least a portion of the user's face,
processing the comparison image and comparing the comparison image to the baseline model,
determining at least one corrective cosmetic recommendation based upon comparing the comparison image to the baseline model, and
displaying at least one overlay upon the comparison image in a location corresponding to the corrective cosmetic recommendation.

13. The method as recited in claim 12 further comprising defining the property of the user's skin as comprising a wrinkle.

14. The method as recited in claim 12 further comprising defining the property of the user's skin as comprising at least one of a wrinkle, a line, a circle, a spot or a pore.

15. The method as recited in claim 12 wherein defining the cosmetic analysis further comprises:
receiving, from the mobile user device, a baseline image of at least a portion of the user's face, the baseline image representing the user's desired application of cosmetics to the user's face,
presenting, to the mobile user device, a plurality of model images, each of the plurality of model images representing different applications of cosmetics to at least one model face,
receiving, from the mobile user device, a selection of at least one of the plurality of model images representing a desired application of cosmetics to the model face,
processing the baseline image for cosmetic application to the user's face shown therein,
processing the selected one of the plurality of model images for cosmetic application to the model face shown therein,
creating the baseline model using at least the determined cosmetic application to the user's face shown in the baseline image and the determine cosmetic application to the selected one of the plurality of model images, and
saving the baseline model to a profile associated with the user.

16. The method as recited in claim 15 further comprising defining the at least one corrective cosmetic recommendation as comprising an instruction to apply an identified cosmetic to an identified portion of the user's face represented on the comparison image.

17. The method as recited in claim 16 further comprising defining the at least one corrective cosmetic recommendation as comprising an instruction to apply a cosmetic technique to an identified portion of the user's face represented on the comparison image.

* * * * *